United States Patent [19]

Yamada et al.

[11] Patent Number: 5,362,497
[45] Date of Patent: Nov. 8, 1994

[54] TRANSDERMAL THERAPEUTIC COMPOSITION

[75] Inventors: Masayuki Yamada, Kawanishi; Muneo Nonomura, Suita; Kohei Nishikawa, Kyoto, all of Japan

[73] Assignee: Takeda Chemical Industries, Ltd., Japan

[21] Appl. No.: 820,020

[22] Filed: Jan. 13, 1992

Related U.S. Application Data

[63] Continuation of Ser. No. 524,870, May 18, 1990, abandoned.

[30] Foreign Application Priority Data

May 25, 1989 [JP] Japan .................................. 1-133364

[51] Int. Cl.⁵ .......................... A61K 9/70; A61F 13/15
[52] U.S. Cl. .................................... 424/449; 424/443; 424/445; 424/447; 424/484; 424/485; 424/487; 424/488; 514/777; 514/781; 514/944; 514/946; 514/953; 514/964
[58] Field of Search ............... 424/443, 445, 447, 449, 424/484, 485, 487, 488; 514/777, 781, 944, 946, 953, 964

[56] References Cited

U.S. PATENT DOCUMENTS

| 4,656,188 | 4/1987  | Veber et al.    | 514/423 |
| 4,748,160 | 5/1988  | Bennion et al.  | 514/443 |
| 4,789,547 | 12/1988 | Song et al.     | 424/449 |
| 4,879,119 | 11/1989 | Konno et al.    | 424/449 |

FOREIGN PATENT DOCUMENTS

| 0043738 | 1/1982  | European Pat. Off. ............ 514/947 |
| 0104037 | 3/1984  | European Pat. Off. . |
| 0127426 | 12/1984 | European Pat. Off. . |
| 0127468 | 12/1984 | European Pat. Off. . |
| 0156455 | 10/1985 | European Pat. Off. . |
| 0171742 | 2/1986  | European Pat. Off. . |
| 3305689 | 8/1984  | Germany ............................ 424/449 |

Primary Examiner—Thurman K. Page
Assistant Examiner—Carlos Azpuru
Attorney, Agent, or Firm—Wegner, Cantor, Mueller & Player

[57] ABSTRACT

When a transdermal therapeutic composition which contains a pharmaceutically effective ingredient, a water-soluble absorption enhancer, a fat-soluble absorption enhancer and a super water-absorbent resin is applied to the skin of mammals, release of the pharmaceutically effective ingredient and the absorption enhancers is controlled and the pharmacological action lasts for a long period of time.

13 Claims, No Drawings

TRANSDERMAL THERAPEUTIC COMPOSITION

This application is a continuation of U.S. application Ser. No. 07/524,870 filed May 18, 1990, now abandoned.

INDUSTRIAL FIELD OF UTILIZATION

This invention relates to a transdermal therapeutic composition which comprises (i) a pharmaceutically effective ingredient, (ii) a water-soluble substance enhancing transdermal absorption of the pharmaceutically effective ingredient, (iii) a fat-soluble substance enhancing transdermal absorption of the pharmaceutically effective ingredient, and (iv) a super water-absorbent resin.

PRIOR ART

Recently, there has been a great interest in a transdermal therapeutic system (TTS) which is a system designed to deliver a drug through the skin to implement the intended systemic effect, and several preparations have already been developed. Thus, nitroglycerol and isosorbide dinitrate, which are antianginal drugs, and clonidine which is a hypotensive agent have been available in TTS preparations. Since drugs such as nitroglycerol mentioned above are per se readily absorbed through the skin and exhibit pharmaceutical effects at a relatively low concentration in blood, they can be formulated without great difficulties. On the other hand, since most of the drugs are poorly absorbed transdermally, it is necessary to enhance their transdermal absorption. As the method of enhancing the absorption, mention is made of a method comprising incorporation of an absorption enhancer or a method resorting to iontophoresis or supersonic waves. While intensive studies on the promotion of transdermal absorption with the aid of an absorption enhancer have been made, no satisfactory result has been obtained yet. Several research efforts have been reported so far, and, among them, the present inventors reported that multi-ingredient absorption enhancers containing one or more species of fat-soluble substances promoting transdermal absorption of a pharmaceutically effective ingredient, such as an aliphatic carboxylic acid, its lower alcohol ester and an aliphatic alcohol (hereinafter sometimes abbreviated as fat-soluble absorption enhancers) and one or more species of water-soluble substances promoting transdermal absorption of a pharmaceutically effective ingredient, such as an alkane polyol (hereinafter sometimes abbreviated as water-soluble absorption enhancers) are excellent in the absorption-enhancing effect and produce less irritation of the skin. These ingredients have been used previously and been considered preferable (cf. the specification of Japanese Patent Application No. 63-222081).

The amounts of these multi-ingredient absorption-enhancers are experimentally determined in accordance with the properties of drugs or their concentrations in blood. However, in the design and production of transdermal therapeutic compositions, there are encountered various problems caused by incorporation of these multi-ingredient absorption-enhancers. For example, problems with compatibility between the above-mentioned fat-soluble absorption-enhancers and water-soluble ones are mentioned. These are substantially incompatible, and, especially in the case of tapes, poor compatibility between the adhesive and the absorption-enhancers thus employed often makes it impossible to prepare intended tapes or, even if intended tapes could be prepared, separation often occurs with the lapse of time. Further, in the case of preparing plasters, water-soluble ingredients including water and fat-soluble ingredients are, in most cases, incorporated. Even in these cases, compatibility is a problem. For solving such problems as mentioned above, there has been known a method comprising incorporation of a surfactant or a polymer, such as polyvinyl pyrrolidone, having a surface-active property. However, depending on the properties or amounts of absorption-enhancers these surfactants or polymers often do not work effectively. Therefore, transdermal absorption of a pharmaceutically effective ingredient is not performed as designed, so as to display only insufficient pharmacological actions, which is a problem to be solved.

PROBLEMS THAT THE INVENTION IS TO SOLVE

The present inventors unexpectedly found that, in the design and preparation of a transdermal therapeutic composition such as a plaster (tape) containing a pharmaceutically effective ingredient and a multi-ingredient absorption-enhancer comprising a water-soluble one and fat-soluble one, separation of the fat-soluble ingredient from the water-soluble ingredient and separation of these ingredients from an adhesive are suppressed by incorporating a super water-absorbent resin into the composition. The present inventors also determined that a homogeneous transdermal therapeutic composition of which the stability with the lapse of time is improved can be obtained, and they conducted further research work and completed the present invention.

MEANS OF SOLVING THE PROBLEM

The present invention provides, as mentioned hereinbefore, a transdermal therapeutic composition which comprises (i) a pharmaceutically effective ingredient;
(ii) a water-soluble substance enhancing transdermal absorption of the pharmaceutically effective ingredient;
(iii) a fat-soluble substance enhancing transdermal absorption of the pharmaceutically effective ingredient; and
(iv) a super water-absorbent resin. The "ingredient (i)", which is the pharmaceutically active ingredient to be used for the transdermal therapeutic composition of this invention, is preferably, taking the design of the composition into consideration, a drug having such a property as poor transdermal absorbability, but any one can be used so long as it is expected to exhibit systemic action through transdermal absorption. Practical examples of such drugs as above include cardiovascular drugs (e.g. angiotensin I converting enzyme inhibitors such as (R)-3-[(S)-1-carboxy-5-(4-piperidyl)pentyl]amino-4-oxo-2,-3,4,5-tetrahydro-1,5-benzothiazepin-5-acetic acid (hereinafter sometimes referred to as Compound (I)) [cf: JP-A-60-231668], Delapril and Captopril; adrenaline $\beta$-receptor blockers such as pindolol and propranolol; adrenaline $\alpha_2$-receptor agonists such as clonidine; Ca antagonists such as nifedipine; and other hypotensive agents; coronary vasodilators such as nitroglycerol, isosorbide dinitrate and molsidomine; cardiotonic glycosides such as digoxin; peripheral vasodilators such as cyclandelate; and cerebral vasoactive agent such as vinpocetine, drugs for cerebral nerves system (e.g. neurotropic drugs such as diazepam and imipyramine; drugs for autonomic nerve system such as dl-methylephedrine hydrochloride; drugs for antivertigo such as diphenhydramine; antipyretics and analgesics such as salicylic acid), drugs for respiratory diseases (e.g. bronchodilators such as epinephrine), drugs for digestive diseases (e.g. digestive canal antispasmodics such as scoporamine), drugs for endocrinic metabolism (e.g. antarthritics such as indomethacin; vitamins such as vitamin D and vitamin E; polypeptide hormones such as LH-RH and TRH; androgens such as testosterone; estrogens such as estradiol; adrenal cortical steroids such as corticosteroid), and anti-tumor drugs (e.g. 5-fluorouracil). These drugs can be incorporated in an optional amount, and the amount varies with the kind of drug and the purpose of use, etc., but an amount of 0.1 to 20% (W/W) is usually preferable. The drugs may be either water-soluble or fat-soluble, and two or more of such drugs can be incorporated into a transdermal therapeutic composition so long as they do not cause undesirable effects by interaction among them.

As the super water-absorbent resin "ingredient (iv)", mention is made of such resins which are capable of absorbing water of several tens to more than one thousand times as much as its own weight, forming a hydrogel by swelling with water and not releasing water even under elevated pressure. Practical examples include saponified vinyl acetate-acrylic acid ester copolymers, polyacrylates, cross-linked polyvinyl alcohol-maleic anhydride copolymers, cross-linked isobutylene-maleic acid copolymers, saponified polyacrylonitrile graft polymers, starch-acrylic acid graft polymers. Among them, polymers which are capable of absorbing water of about 50 to 2000 times as much as their own weight are preferable. The amount of a super water-absorbent resin to be incorporated into a transdermal therapeutic composition is optional, but, preferably, about 0.1 to 10% (W/W), more preferably, about 0.5 to 5% (W/W).

The fat-soluble substance enhancing the transdermal absorption of the pharmaceutically effective ingredient (fat-soluble absorption enhancer), which is used as "ingredient (iii)", includes, for example, aliphatic carboxylic acids containing 6 to 20 carbon atoms, lower alcohol esters thereof and aliphatic alcohols containing 6 to 20 carbon atoms.

The aliphatic carboxylic acids containing 6 to 20 carbon atoms include, among others, saturated or unsaturated aliphatic monocarboxylic acids and dicarboxylic acids, such as caproic acid, caprylic acid, captic acid, lauric acid, myristic acid, palmitic acid, stearic acid, arachic acid, decenoic acid, linderic acid, oleic acid, linoleic acid, linolenic acid, arachidonic acid, and sebacic acid. The lower alcohol esters of aliphatic carboxylic acids containing 6 to 20 carbon atoms include esters of the above-mentioned aliphatic carboxylic acids with lower alcohols containing 1 to about 5 carbon atoms (for example, methanol, ethanol, propanol, 2-propanol, butanol, pentanol). The lower alcohol esters of aliphatic dicarboxylic acid include the mono- or diesters formed as one or both of the available carboxyl groups are esterified. As examples of a lower alcohol ester of an aliphatic carboxylic acid containing 6 to 20 carbon atoms, there may be mentioned diethyl sebacate, isopropyl myristate and so on.

The aliphatic alcohols containing 6 to 20 carbon atoms include saturated and unsaturated aliphatic alcohols such as caproyl alcohol, caprylyl alcohol, capryl alcohol, lauryl alcohol, myristyl alcohol, cetyl alcohol, stearyl alcohol, oleyl alcohol, linoleyl alcohol, and linolenyl alcohol.

Preferred, among the aliphatic carboxylic acids, lower alcohol esters thereof and aliphatic alcohols, is an ester of an aliphatic monocarboxylic acid with a lower ($C_{1-5}$) alcohol. The most desirable is isopropyl myristate.

As the water-soluble substance enhancing transdermal absorption of the pharmaceutically effective ingredient (water-soluble absorption enhancer) [ingredient (ii)], mention is made of, for example, an alkanepolyol, etc.

The alkanepolyol includes, among others, lower alkanediols containing about 2 to 5 carbon atoms, such as ethylene glycol (1,2-ethanediol), propylene glycol (1,2-propanediol), 1,3-propanediol, 1,2-butanediol, 1,3-butanediol, 1,4-butanediol, 2,3-butanediol and 1,5-pentanediol, and lower alkanetriols containing about 2 to 5 carbon atoms, such as glycerol. Particularly preferred are propylene glycol and 1,3-butanediol.

The above-mentioned absorption enhancer consists of one or more species of fat-soluble absorption enhancers and one or more species of water-soluble absorption enhancers. The proportion of fat-soluble absorption enhancers and water-soluble enhancers in the transdermal therapeutic composition is virtually optional, but preferably in the range of about 0.1 to 80% (W/W), more preferably about 1 to 50% (W/W).

The aliphatic carboxylic acid or the aliphatic alcohol, which is used as ingredient (iii), is used in a proportion of, preferably, about 0.5 to 10% (W/W) and, for still better results, about 0.5 to 5% (W/W) based on the total weight of the composition. The lower alcohol ester of an aliphatic carboxylic acid, which may also be used as ingredient (iii), is used in a proportion of, preferably, about 1 to 50% (W/W) and, for still better results, about 5 to 30% (W/W) on the same basis. When two or more kinds of aliphatic carboxylic acids, lower alcohol esters of aliphatic carboxylic acids or aliphatic alcohols are used, the total amount of the aliphatic carboxylic acids is preferably about 0.5 to 20% (W/W) and, for still better results, about 0.5 to 10% (W/W), the total amount of the lower alcohol esters of aliphatic carboxylic acids is preferably about 1 to 50% (W/W) and, for still better results, about 5 to 30% (W/W), and the total amount of the aliphatic alcohols is preferably about 0.5 to 20% (W/W) and, for still better results, about 0.5 to 10% (W/W).

The proportion of the alkanepolyol in this transdermal therapeutic composition, which is used as ingredient (ii), is preferably about 1 to 50% (W/W), for still better results, about 1 to 30% (W/W).

For insuring more uniform blending of the ingredients of this transdermal therapeutic composition, a nonionic surfactant is preferably incorporated.

The nonionic surfactant includes, among others, polyoxyethylene sorbitan fatty acid esters (for example, polyoxyethylene sorbitan monooleate, polyoxyethylene sorbitan monostearate, polyoxyethylene sorbitan monopalmitate, polyoxyethylene sorbitan monolaurate, etc.), polyoxyethylene sorbitol fatty acid esters (for example, polyoxyethylene sorbitol monolaurate etc.), polyoxyethylene fatty acid esters (for example, polyoxyethylene stearate etc.), polyoxyethylene higher alcohol ethers (for example, polyoxyethylene lauryl alcohol, polyoxyethylene oleyl alcohol, etc.), polyoxyethylene alkylaryl ethers (for example, polyoxyethylene nonylphenol etc.), polyoxyethylene castor oil. derivatives (for example, polyoxyethylene hydrogenated castor oil derivatives such as HCO-50, and HCO-60, etc.), polyoxyethylene lanolin derivatives, polyoxyethylene lanolin alcohol. derivatives, and block polymer nonionic surfactants (for example, Pluronic L-62, L-64, F-68, etc.). The proportion of the nonionic surfactant(s) of which the HLB value ranges from 5 to 20 is optional based on the total composition, but preferably about 0.5 to 20% and, for better results, about 0.5 to 10%, and for still better results, about 1 to 5% (W/W).

The transdermal therapeutic composition of this invention may further contain an inorganic base. Examples of the inorganic base include alkali metal hydroxides (e.g. sodium hydroxide, potassium hydroxide) , alkali metal hydrogencarbonate (e.g. sodium hydrogencarbonate, potassium hydrogencarbonate ) , etc. The amount of the inorganic base to be added varies with the kinds of inorganic bases to be employed, but it ranges generally from 0.02 to 5% (W/W) so that the pH of the resulting composition may be in the range of from 6 to 9. In the case that an alkali metal hydroxide or an alkali metal hydrogencarbonate is used as the inorganic base, the amount usually ranges from about 0.8 to about 1.2 mole relative to 1 mole of the pharmaceutically effective ingredient, and, in the case that an alkali metal carbonate is used as the inorganic base, the amount usually ranges from about 0.4 to about 0.6 mole relative to 1 mole of the pharmaceutically effective ingredient. Besides the above-mentioned inorganic bases, an acid such as hydrochloric acid, citric acid or the like may be further added. These are added for dissolving the pharmaceutically effective ingredient, and, therefore, the amount to be added is optional.

The transdermal therapeutic composition of this invention is provided in such dosage forms as patch, cataplasma, ointment (inclusive of cream), hard ointment, tape, suppository, lotion, solution, suspension, emulsion and aerosol mist. Among them, transdermal therapeutic plasters (e.g. patch, cataplasma, hard ointment, tape, etc.) are preferable. The ointment (inclusive of cream), suppository, lotion, solution, suspension, emulsion and aerosol can be manufactured by formulating the above-mentioned ingredients (i), (ii), (iii) and (iv), and, if necessary, the nonionic surfactant, inorganic base and acid, with a solvent, suspending agent, emulsifier, propellant, ointment base, suppository base, or the like, which are well known in pharmaceutical industry. If necessary, a preservative (for example, ethyl p-hydroxybenzoate, benzalkonium chloride), antiphlogistic agent (for example, glycyrrhizinoic acid), etc. can be further incorporated. The plasters such as patch, cataplasma, hard ointment and tape can be manufactured by mixing the above-mentioned ingredients (i), (ii), (iii) and (iv), and, when necessary, the nonionic surfactant, inorganic base or acid, with a base which is well known in pharmaceutical industry and, if necessary, after addition of a preservative, an antiphlogistic agent, etc., subjecting the mixture to absorption into, or adhesive to, an appropriate support material. The support material may be a high polymer film, a web of woven or nonwoven fabric, a sheet of paper or the like. The adhesive agent to be used in the manufacture of the patch, cataplasma or tape includes, among others, polyalkyl vinyl ether, polyalkyl acrylate (JP-B-58-23846), polyisobutylene, natural rubber and synthetic rubber adhesives. For assuring suitable plasticity and tackiness, animal oil (for example, squalene, squalane, etc.) or vegetable oil (for example, olive oil, jojoba oil, etc.), petrolatum, lanolin, etc. may be added.

In the manufacture of the ointment, hard ointment, suppository, tape, patch and cataplasma, there may be incorporated ingredients for modulating the transdermal absorption, such as lecithin and other phospholipids, solid paraffin, bees-wax, carnauba wax, hydrogenated castor oil, lanolin, petrolatum, polyvinyl alcohol, polyvinylpyrrolidone, polyethylene glycol, glycerol fatty acid ester, cholesterol, Carbopol, carboxymethylcellulose, carboxyethylcellulose, silicone resin and a lower alcohol (for example, ethanol, isopropyl alcohol, etc.).

The solvent includes, among others, water, ethanol and glycerol. The suspending agent and emulsifying agent include, among others, gum arabic, carboxymethylcellulose, methylcellulose and sodium alginate. The aerosol propellant includes, among others, non-combustible liquefied gases (for example, freon 11, freon 12, freon 113, etc.). The ointment base includes, among others, petrolatum, solid paraffin, vegetable oil, animal oil, mineral oil, lanolin, waxes, and macrogols. The hard ointment includes, among others, bees-wax, paraffin, macrogols and glycerol fatty acid esters. The suppository base includes, among others, cacao butter, lanolin fat, macrogols, Witepsol and glycerogelatin.

The application of the transdermal therapeutic composition of this invention depends on symptoms of the subject. When compound (I) is applied to an adult human for the treatment of hypertension, about 1 to 200 mg, preferably about 10 to 150 mg, of compound (I) which is used as the pharmaceutically effective ingredient is used in a single dosage form and applied once in 1 to 7 days, preferably once a day (by sticking, coating, spraying or insertion into the rectum). And, when plasters are used, they may be applied to any part of the body.

The mixing of the respective ingredients and the manufacture of a transdermal therapeutic composition can be performed by the per se known procedures such as those described in the Japanese Pharmacopeia.

In case that ingredient (i) is a substance which can be dissolved in water in the presence or absence of an inorganic base or an acid or a substance which can be dissolved in ingredient (ii), it is preferable that ingredients (i), (ii) and (iv) are first mixed in the presence of water so that ingredients (i) and (ii) with water can be absorbed into ingredient (iv), and that the obtained mixture is then dispersed in ingredient (iii) or a mixture of ingredient (iii) and a nonionic surfactant. Ingredient (iii) or a mixture of ingredient (iii) and a nonionic surfactant can be dissolved in a suitable organic solvent (e.g. ethyl acetate) before use. After dispersion, the obtained mixture is subjected to drying, if necessary.

When ingredient (i) is a fat-soluble substance, it is preferable that ingredient (ii) and water are first absorbed into ingredient (iv) and that the obtained mixture is then dispersed in a mixture of ingredients (i) and (iii) or a mixture of ingredients (i) and (iii) and a nonionic surfactant. A mixture of ingredients (i) and (iii) or a mixture of ingredients (i) and (iii) with a nonionic surfactant can be dissolved in a suitable organic solvent (e.g. ethyl acetate) before use. After dispersion, the obtained mixture is subjected to drying, if necessary.

ACTIONS AND EFFECTS

In the transdermal therapeutic composition of this invention, due to incorporation of a super water-absorbent resin, no separation of the ingredients from one another occurs. Therefore, release of the pharmaceutically effective ingredient and the absorption enhancers is controlled, and transdermal absorption of the pharmaceutically effective ingredient as designed is observed and the pharmacological action lasts for a sufficiently long period of time. Therefore, the transdermal therapeutic composition of this invention can be applied to the skin of mammals (for example, human, monkey, dog, cat, etc.) as a prophylactic and therapeutic agent for various diseases.

EXAMPLES

The following examples are intended to illustrate the present invention in further detail and should not be construed as limiting the scope of the invention.

Example 1

[Preparation of a transdermal therapeutic plaster]

First, an aqueous phase was prepared by mixing and dissolving 10 g of Compound (I), i.e. (R)-3-[(S)-1-carboxy-5-(4-piperidyl)pentyl]amino-4-oxo-2,3,4,5-tetrahydro-1,5-benzothiazepine-5-acetic acid, an angiotensin converting enzyme inhibitor, 50 ml of water, 20 g of propylene glycol, 1.15 g of NaOH and 1 g of a super water-absorbent resin [a vinyl acetate-acrylic acid ester copolymer hydrolyzate (Sumikagel SP-510, manufactured by Sumitomo Chemical Co., Ltd.)]. On the other hand, an oily phase was prepared by mixing and dissolving, in ethyl acetate, 43 g of a purified polymer fraction of polyalkyl acrylate adhesive [methyl acrylate-2-ethylhexyl acrylate copolymer emulsion, Nikasol TS-620, manufactured by Nippon Carbide Industries, Co., Ltd.], 5 g of Tween 80 and 20 g of isopropyl myristate. The above aqueous and oily phases were combined and mixed well, and a polyethylene sheet was coated with the mixture in a coverage corresponding to a dry thickness of about 100 μm and dried at 80° C. for 5 minutes. After drying, the coated sheet was covered with a separator (a release sheet) to provide a transdermal therapeutic plaster (tape).

[Transdermal absorption test]

Using 9-week-old male SD rats, the transdermal therapeutic tape (6 mg as compound (I)/rat) was applied to a clipped area (6 $cm^2$) of the abdominal skin and the area of exposure was covered by the occluded dressing method. The transdermal absorption effect was evaluated daily by monitoring the inhibition rate (%) against hypertensive reaction induced by angiotensin I. Angiotensin I was administered in an intravenous dose of 300 ng/kg (rats). The degree and duration of absorption were evaluated using, as indexes, initiation and duration time of inhibition of not less than 80% against hypertensive reaction induced by anglotension I after the tape was administered.

[Results]

The transdermal therapeutic tape thus prepared had smooth surface and uniform thickness, without causing separation of the absorption on enhancers and the adhesive even after storage at 40° C. for three months or at room temperature for six months . The compound (I) was sufficiently absorbed transdermally, and 80% inhibition against hypertensive reactivity induced by angiotensin I was observed five hours after the administration and this effect lasted for longer than 24 hours .

Example 2

[Preparation of a transdermal therapeutic plaster]

First, an aqueous phase was prepared by mixing and dissolving 15 g of the same Compound (I) as used in Example 1, 70 ml of water, 15 g of propylene glycol, 10 g of 1,3-butylene glycol, 1.15 g of NaOH and 2 g of a super water-absorbent resin [a vinyl acetate-acrylic acid ester copolymer hydrolyzate, Sumikagel SP-510, Sumitomo Chemical Co., Ltd.]. On the other hand, an oily phase was prepared by dissolving, in ethyl acetate, 38 g of polyalkyl vinyl ether adhesive [polyvinyl ethyl ether (Tg:−30° C.)/polyvinyl ethyl ether (Tg:−60° C.)=60parts/40 parts], 5 g of Tween 80 and 15 g of isopropyl myristate. The above aqueous and oily phases were combined and mixed well, and a polyethylene sheet was coated with the mixture in the coverage corresponding to a dry thickness of about 100 μm and dried at 100° C. for 3 minutes. After drying, the coated sheet was covered with a separator to provide a transdermal therapeutic plaster (tape).

[Transdermal absorption test]

The test procedure described in Example 1 was followed.

[Results]

The transdermal therapeutic tape thus prepared had a smooth surface and uniform thickness, without causing separation of the absorption enhancers and the adhesive even after storage at 40° C. for three months or at room temperature for six months. The compound (I) was sufficiently absorbed transdermally, and 80% inhibition against hypertensive reaction by angiotensin I was observed three hours after the administration and this effect lasted for longer than 24 hours.

Example 3

[Preparation of a transdermal therapeutic plaster]

First, an aqueous phase was prepared by mixing and dissolving 10 g of the same Compound (I) as used in Example 1, 50 ml of water, 20 g of propylene glycol, 1.15 g of NaOH and 1 g of a super water-absorbent resin [polyacrylate, Sumikagel NP-1010, Sumitomo Chemical Co., Ltd.]. On the other hand, an oily phase was prepared by mixing and dissolving, in ethyl acetate, 50 g of a purified polymer fraction of a polyalkyl acrylate adhesive [methyl acrylate-2-ethylhexyl acrylate copolymer emulsion, Nikasol TS-620, Nippon Carbide Industries, Co., Ltd.], 8 g of Tween 20 and 10 g of oleyl alcohol. The above aqueous and oily phases were combined and mixed well, and a polyethylene sheet was coated with the mixture in a coverage corresponding to a dry thickness of about 100 μm and dried at 80° C. for 5 minutes. After drying, the coated sheet was covered with a separator to provide a transdermal therapeutic plaster (tape).

[Transdermal absorption test]

The test procedure described in Example 1 was followed.

[Results]

The transdermal therapeutic tape thus prepared had smooth surface and uniform thickness, without causing separation of the absorption enhancers and the adhesive even after storage at 40° C. for three months or at room temperature for six months. The compound (I) was sufficiently absorbed transdermally, and 80% inhibition against hypertensive reaction by angiotensin I was observed five hours after the administration and this effect lasted for longer than 24 hours.

Example 4

[Preparation of a transdermal therapeutic plaster]

An aqueous phase was prepared by mixing and dissolving 15 g of such Compound (I), 30 ml of water, 20 g of propylene glycol, 1.3 g of NaOH and 1 g of a super water-absorbent resin [a vinyl acetate-acrylic acid ester copolymer hydroclyzate (Sumikagel SP-510, manufactured by Sumitomo Chemical Co., Ltd.)]. On the other hand, an oily phase was prepared by mixing and dissolving, in ethyl acetate, 37.7 g of a polyalkyl acrylate adhesive [a copolymer prepared by polymerization of 55 weight parts of 2-ethylhexyl acrylate, 30 weight parts of methoxyethyl acrylate and 15 weight parts of vinyl acetate using ethyl acetate as a Solvent], 5 g of Tween 80 and 20 g of isopropyl myristate. The above aqueous and oily phases were combined and mixed well, and a polyethylene sheet was coated with the mixture in a coverage corresponding to a dry thickness of about 100 μm and dried at 70° C. for 5 minutes. After drying, the coated sheet was covered with a separator (a release sheet) to provide a transdermal therapeutic plaster (tape).

[Transdermal absorption test]

Using 9-week-old male SD rats, the transdermal therapeutic tape (9 mg as compound (I)/rat) was applied to a clipped area (6 cm²) of the abdominal skin and the area of exposure was covered by the occluded dressing method. The test procedure described in Example 1 was followed.

[Results]

The transdermal therapeutic tape thus prepared had a smooth surface and uniform thickness, without causing separation of the absorption enhancers and the adhesive even after storage at 40° C. for three months or at room temperature for six months. The compound (I) was sufficiently absorbed transdermally, and 80% inhibition against hypertensive reactivity by angiotensin I was observed five hours after the administration and this effect lasted for longer than 24 hours.

Example 5

[Preparation of transdermal therapeutic composition]

In a mixture of 16 g of propylene glycol and 5 g of water was dissolved 5 g of molsidomine (N-ethoxycarbonyl-3-morpholinosydnonimine), and 1 g of Sumikagel SP-510 was further added. The mixture was homogeneously mixed with a homogenizer, and then 3 g of polysorbate 80 and 5 g of oleic acid were added. The resulting mixture was emulsified with a homogenizer, and 0.35 g of the emulsion was absorbed into a rayon web of nonwoven fabric and put into a silicone chamber having an area of 3 cm² and a depth of 1 mm, to provide a transdermal therapeutic composition.

[Therapeutic absorption test]

The above transdermal therapeutic composition was put on a clipped abdomen of male SD rats (7-week-old, 240 to 270 g, 5 heads) and fixed with a surgical tape. After 1, 2, 4, 6 and 24 hours, the blood was collected from the tail vein, and the concentration of molsidomine in the plasma was determined by HPLC.

[Results]

As shown in Table 1, molsidomine was sufficiently absorbed that a high concentration of molsidomine in the blood was observed.

TABLE 1

| Elapsed time after administration (h) | Average concentration in plasma (ng/ml) |
|---|---|
| 1 | 123.0 |
| 2 | 234.9 |
| 4 | 451.4 |
| 6 | 321.6 |
| 24 | 169.2 |

On the other hand, 0.5 g of molsidomine was dissolved in 3 g of propylene glycol, and 0.35 g of the solution was absorbed into a rayon web of nonwoven fabric and applied to SD rats in the same manner as mentioned above. The concentration of molsidomine in the plasma was below the detection limit.

Example 6

[Preparation of transdermal therapeutic composition]

In a mixture of 20 g of propylene glycol and 5 g of water was dissolved 9 g of TRH (L-pyroglutamyl-L-histidyl-L-prolinamide), and 1 g of Sumikagel SP-510 was further added. The mixture was homogeneously mixed with a homogenizer, and then 5 g of polysorbate 80 was added. The mixture was homogeneously mixed with a homogenizer, and 20 g of isopropyl myristate were added. The resulting mixture was emulsified with a homogenizer, and 0.35 g of the emulsion was absorbed into a rayon web of nonwoven fabric and put into a silicone chamber having an area of 3 cm² and a depth of 1 mm, to provide a transdermal therapeutic composition.

[Therapeutic absorption test]

The above transdermal therapeutic composition was put on a clipped abdomen of male SD rats (7-week-old, 240 to 270 g, 4 heads) and fixed with a surgical tape. After 0.5, 1, 2, 4, 6 and 24 hours, the blood was collected from the tail vein. After the blood was treated with heparin, 50 μl of a reagent (aqueous solution containing 0.01 g/l of 8-hydroxyquinoline sulfate, 0.15 g/l of EDTA-2Na and 0.05 g/l of Tween 20) was added to 0.5 ml of the blood to separate the plasma. The TRH concentration in the plasma was determined by the below-mentioned radioimmunoassay. To 100 μl of the separated plasma were added 100 μl of 0.7% bovine serum albumin, 100 μl of anti-TRH antibody (500-fold dilution) and 100 μl of $^{125}$I-labeled TRH (about 10000 dpm), and the resulting mixture was incubated at 4° C. for 3 days. The secondary antibody (100 μl of anti-γ-globulin serum and 100 μl of normal rabbit serum) was then added, and the mixture was incubated at 4° C. for 1 day. The supernatant was removed by centrifugation at 3000 rpm, and the radioactivity of the precipitate was determined by a γ counter.

[Results]

As shown in Table 2, the TRH concentration in the plasma rapidly increased, and the maximum concentration (about 400 ng/ml) was observed 4 hours after the administration. Even after 24 hours, a high concentration of TRH was maintained (82.4 ng/ml).

TABLE 2

| Elapsed time after administration (h) | Average concentration in plasma (ng/ml) |
|---|---|
| 0.5 | 59.0 |
| 1 | 88.9 |
| 2 | 110.0 |
| 4 | 391.3 |
| 6 | 325.7 |

TABLE 2-continued

| Elapsed time after administration (h) | Average concentration in plasma (ng/ml) |
|---|---|
| 24 | 82.4 |

On the other hand, 10% polyvinyl alcohol gel (pH 4, buffered with 0.01M citric acid-0.01M disodium phosphate) containing 2% TRH was formulated to make the diameter and thickness 3.2 cm and 0.1 cm respectively (sticking area: 8 cm$^2$; TRH content: 16 mg), and applied to SD rats (4 heads) in the same manner as mentioned above. The TRH concentration in the plasma was determined by the radioimmunoassay in the same manner as mentioned above. As shown in Table 3, the TRH concentration was very low.

TABLE 3

| Elapsed time after administration (h) | Average concentration in plasma (ng/ml) |
|---|---|
| 0.5 | 8.3 |
| 1 | 8.0 |
| 2 | 4.5 |
| 4 | 3.0 |
| 6 | 1.8 |

Example 7

[Preparation of transdermal therapeutic composition]

In 5 g of 1N hydrochloric acid was dissolved 2.15 g of vinpocetine (apovincamic acid ethyl ester), and 1 g of Sumikagel SP-510 was added. The mixture was homogeneously mixed with a homogenizer, and then 20 g of propylene glycol and 5 g of polysorbate 80 were added. The resulting mixture was homogeneously mixed, and then 20 g of isopropyl myristate was added. The resulting mixture was emulsified with a homogenizer, and 0.35 g of the emulsion was absorbed into a rayon web of nonwoven fabric and put into a silicone chamber having an area of 3 cm$^2$ and a depth of 1 mm to prepare a transdermal therapeutic composition.

[Transdermal absorption test]

The above transdermal therapeutic composition was put on a clipped abdomen of male SD rats (7-week-old, 240 to 270 g, 4 heads) and fixed with a surgical tape. Just before the administration and after 0.5, 1, 2, 4, 6 and 24 hours, the blood was collected from the tail vein. After the blood was treated with heparin, the plasma was separated. The concentration of vinpocetine in the plasma was determined by HPLC after the plasma was cleaned up by Sep-Pak C18 (Waters).

[Results]

As shown in Table 4, the concentration of vinpocetine in the plasma rapidly increased, and the required concentration was maintained during a period of 24 hours.

TABLE 4

| Elapsed time after administration (h) | Average concentration in plasma (ng/ml) |
|---|---|
| Just before adminstration | 0 |
| 0.5 | 149.3 |
| 1 | 155.4 |
| 2 | 80.1 |
| 4 | 60.7 |
| 6 | 74.1 |
| 24 | 64.3 |

On the other hand, 0.35 g of 4% aqueous suspension of vinpocetine was absorbed into a web of nonwoven fabric and applied to SD rats in the same manner as mentioned above. The concentration of vinpocetine in the plasma was below the detection limit.

What is claimed is:

1. A transdermal therapeutic composition which comprises:
   (i) 0.1 to 20% of a pharmaceutically effective ingredient;
   (ii) 1 to 50% (w/w) water-soluble substance which enhances transdermal absorption of the pharmaceutically effective ingredient;
   (iii) 0.1 to 80% (w/w) fat-soluble substance which enhances transdermal absorption of the pharmaceutically effective ingredient; and
   (iv) 0.1 to 10% (w/w) vinyl acetate-acrylic acid ester copolymer hydrolyzate capable of absorbing about 50 to 2000 times its own weight of water, whereby upon contact with said water swells to form a hydrogel.

2. A transdermal therapeutic composition according to claim 1, wherein the transdermal absorption-enhancing water-soluble substance is an alkanediol containing 2 to 5 carbon atoms or an alkanetriol containing 2 to 5 carbon atoms.

3. A transdermal therapeutic composition according to claim 1, wherein the transdermal absorption-enhancing water-soluble substance is propylene glycol or 1,3-butanediol.

4. A transdermal therapeutic composition according to claim 1, wherein the transdermal absorption-enhancing fat-soluble substance is an aliphatic carboxylic acid containing 6 to 20 carbon atoms, an ester of an aliphatic carboxylic acid containing 6 to 20 carbon atoms with an alcohol containing 1 to 5 carbon atoms, or an aliphatic alcohol containing 6 to 20 carbon atoms.

5. A transdermal therapeutic composition according to claim 1, wherein the transdermal absorption-enhancing fat-soluble substance is an ester of an aliphatic monocarboxylic acid with an alcohol containing 1 to 5 carbon atoms.

6. A transdermal therapeutic composition according to claim 1, wherein the pharmaceutically effective ingredient is an angiotensin converting enzyme inhibitor, an adrenaline β-receptor blocker, an adrenaline $a_2$-receptor agonist, a calcium antagonist, a coronary vasodilator, a cardiotonic glycoside, a peripheral vasodilator, a cerebral vasoactive agent, a neurotropic drug, a drug for autonomic nerve system, a anti-vertigo drug, an antipyretic, an analgesic, a bronchodilator, a digestive canal antispasmodic, an antarthritic, a vitamin, a polypeptide hormone, an androgen, an estrogen, an adrenal cortical steroid, or an anti-tumor drug.

7. A transdermal therapeutic composition according to claim 1, wherein the pharmaceutically effective ingredient is an angiotensin converting enzyme inhibitor.

8. A transdermal therapeutic composition according to claim 1, wherein the pharmaceutically effective ingredient is (R)-3-[(S)-1-carboxy-5-(4-piperidyl)pentyl]amino-4-oxo-2,3,4,5-tetrahydro-1,5-benzothiazepine-5-acetic acid.

9. A transdermal therapeutic composition according to claim 1, which is in the form of patch, cataplasma, hard ointment or tape.

10. A transdermal therapeutic composition according to claim 1, which contains (i) (R)-3-[(S)-1-carboxy-5-(4piperidyl)pentyl]amino-4-oxo-2,3,4,5-tetrahydro-1,5-benzothiazepine-5-acetic acid, (ii) propylene glycol, (iii)

isopropyl myristate, (iv) a vinyl acetate-acrylic acid ester copolymer hydrolyzate, (v) an inorganic base and water.

11. A transdermal therapeutic composition according to claim 10, wherein the inorganic base is sodium hydroxide.

12. A transdermal therapeutic composition according to claim 1, further comprising a nonionic surfactant present at 0.5 to 20% (w/w).

13. A transdermal therapuetic composition according to claim 1, which is in a form of tape.

* * * * *